United States Patent [19]

Knesel

[11] Patent Number: 5,001,288

[45] Date of Patent: Mar. 19, 1991

[54] HALOETHYLATION OF AROMATIC HYDROCARBONS

[75] Inventor: George A. Knesel, Orangeburg, S.C.

[73] Assignee: Ethyl Corporation, Richmond, Va.

[21] Appl. No.: 395,017

[22] Filed: Aug. 17, 1989

Related U.S. Application Data

[63] Continuation-in-part of Ser. No. 240,155 Aug. 26, 1988, abandoned, which is a continuation-in-part of Ser. No. 240,156, abandoned.

[51] Int. Cl.$^5$ .............................................. C07C 17/00
[52] U.S. Cl. .................................... 570/195; 558/342; 562/496
[58] Field of Search .......................................... 570/195

[56] References Cited

U.S. PATENT DOCUMENTS

| | | | |
|---|---|---|---|
| 2,166,554 | 7/1939 | Roblin | 570/195 |
| 2,516,971 | 8/1950 | Galitzenstein | 260/651 |
| 2,862,980 | 12/1958 | Muench | 570/195 |
| 2,973,391 | 2/1961 | Earhart | 570/195 |
| 3,006,953 | 10/1961 | Grosskinsky | 570/195 |
| 3,422,160 | 1/1969 | Napier | 570/195 |
| 3,658,923 | 4/1972 | Stapp | 570/195 |
| 3,887,484 | 6/1975 | Norwood | 570/261 |
| 4,536,595 | 8/1985 | Gardano | 562/406 |

FOREIGN PATENT DOCUMENTS

1197254 11/1985 Canada .
47-39050 12/1972 Japan .
52-111536 9/1977 Japan .
1560082 1/1980 United Kingdom .

OTHER PUBLICATIONS

March, "Advanced Organic Chemistry", 2nd Ed., pp. 501–502 (1977).
Olah, "Friedel–Crafts and Related Reactions", vol. 2, pp. 659–784 (1964).
Palecek, Czech. Cert. of Authership, 219, 752 (1982).

*Primary Examiner*—Michael L. Shippen
*Attorney, Agent, or Firm*—Richard J. Hammond; Patricia J. Hogan

[57] ABSTRACT

A monoalkylaromatic hydrocarbon is haloethylated to a 1-halo-1-arylethane with minimal co-formation of diarylalkane by-product by reacting it with hydrogen chloride or bromide and acetaldehyde at a temperature in the range of abaout +10° C. to about −35° C. in the presence of at least about 1.4 mols of hydrogen sulfate per mol of the aromatic hydrocarbon and in the absence of more than about 15% by weight of water, based on the weight of the hydrogen sulfate; the temperature being not higher than about −10° C. when hydrogen chloride is employed.

12 Claims, No Drawings

HALOETHYLATION OF AROMATIC HYDROCARBONS

CROSS REFERENCE TO RELATED APPLICATIONS

This application is a continuation-in-part of copending applications Ser. No. 240,155 and Ser. No. 240,156, both filed August 26, 1988, now both abandoned.

FIELD OF INVENTION

This invention relates to a process for haloethylating aromatic hydrocarbons to form 1-halo-1-arylethanes.

BACKGROUND

As disclosed in March, Advanced Organic Chemistry, Second Edition, McGraw-Hill, New York, 1977, pp. 501–502; Olah, *Friedel-Crafts and Related Reactions*, Volume 2, Interscience Publishers, New York, 1963–1964, pp. 659–784; U. S. Pat. No. 2,516,971 (Galitzenstein et al.); and the references cited therein, it is known that aromatic compounds can be haloalkylated by reacting them with a hydrogen halide and an appropriate aldehyde in the presence of a Lewis acid or a proton acid as a catalyst, most commonly in the presence of zinc chloride.

The chloroalkylations utilizing formaldehyde as the aldehyde have been successfully employed in providing fairly high yields of 1-chloro-1-arylalkanes; reasonably high yields of 1-chloro-1-arylalkanes have also been obtained from chloroalkylations utilizing higher aldehydes in some cases, e.g., when the aromatic compound has had an appropriate functional substituent or a plurality of alkyl substituents; and reasonably acceptable, although lower, yields of 1-halo-1-arylalkanes have been obtained in comparable bromoalkylation reactions. However, when the aromatic compound has been a less reactive compound, e.g., an unsubstituted aromatic hydrocarbon or a monoalkylaromatic hydrocarbon, it has not been found possible to provide commercially acceptable yields of 1-halo-1-arylalkane, even when the haloalkylation has been a chloroalkylation rather than a bromoalkylation. There has been too much co-formation of diarylalkane by-product, especially in the bromoalkylation reactions.

Another disadvantage of the known haloalkylation processes utilizing the higher aldehydes has been their providing too much o-isomer in processes performed to provide 1-halo-1(4-alkylphenyl)alkanes, such as the compounds which have been synthesized by other techniques to provide intermediates for ibuprofen, related pharmaceuticals, detergents, etc. It would be desirable to find a way of increasing the para/ortho ratio obtainable from such processes to provide a more economical method of preparing the 1-halo-1-(4-alkylphenyl)alkanes which can be used in known processes, such as those of U. S. Pat. No. 4,536,595 (Gardano et al.), Canadian Patent No. 1,197,254 (Francalanci et al.), British Patent No. 1,560,082 (Dynamit Nobel), Czechoslovakian Certificate of Authorship 219,752 (Palecek et al.), and Japanese Kokai 47-39050 (Miyatake et al.) and 52-111536 (Tokutake).

SUMMARY OF THE INVENTION

An object of this invention is to provide a novel process for haloethylating an aromatic hydrocarbon with hydrogen chloride or bromide and acetaldehyde to form a 1-halo-1-arylethane.

Another object is to provide such a process which minimizes co-formation of a diarylalkane by-product.

Still another object is to provide such a process which maximizes the para/ortho ratio in the product when the aromatic hydrocarbon is a monoalkylbenzene.

A further object is to provide an improved method of preparing 1-halo-1-arylethanes useful as chemical intermediates.

These and other objects are attained by reacting a monoalkylaromatic hydrocarbon with hydrogen chloride or bromide and acetaldehyde at a temperature in the range of about $+10°$ C. to about $-35°$ C. in the presence of at least about 1.4 mols of hydrogen sulfate per mol of the aromatic hydrocarbon and in the absence of more than about 15% by weight of water, based on the weight of the hydrogen sulfate; the temperature being not higher than about $-10.$C when hydrogen chloride is employed.

DETAILED DESCRIPTION

The aromatic hydrocarbon employed in the practice of the invention is a monoalkylaromatic hydrocarbon, such as 1-methylnaphthalene, 2-methylnaphthalene, 9-methylanthracene, 9-butylanthracene, 9-dodecylanthracene, and the various monoalkylbenzenes, e.g., the methyl-, ethyl-, propyl-, isobutyl-, sec-butyl-, t-butyl-, isopentyl-, t-pentyl-, and hexylbenzenes. The most preferred aromatic hydrocarbons are the monoalkylbenzenes wherein the alkyl group contains 1–5 carbons.

The hydrogen halide which is reacted with the aromatic hydrocarbon and acetaldehyde is preferably anhydrous or at least substantially anhydrous. However, some water in the hydrogen halide can be tolerated as long as it is not an amount sufficient to raise the total amount of water in the reaction mixture above about 15% by weight of the hydrogen sulfate, although it is preferred to keep the total amount of water at a concentration not higher than about 10% by weight of the hydrogen sulfate. The hydrogen halide may be incorporated into the reaction mixture per se or as a salt, such as sodium chloride or bromide, which reacts with sulfuric acid to form hydrogen chloride or bromide under the reaction conditions.

The acetaldehyde may be employed per se or may be introduced in the form of a substance, such as paraldehyde, which decomposes to yield acetaldehyde under the reaction conditions.

The aromatic hydrocarbon, hydrogen halide, and acetaldehyde are normally employed in substantially equimolar amounts, but the proportions do not appear to be critical. Thus, amounts of any of the reactants which are smaller or larger than the equimolar amounts may be used if desired.

In order to avoid the presence of an excess of water in the reaction mixture, the hydrogen sulfate is introduced in the form of 85-98% sulfuric acid, preferably sulfuric acid having a concentration of 90-98%, most preferably 93-98%. The amount employed is such as to provide at least about 1.4 mols, preferably at least about 5 mols, per mol of aromatic hydrocarbon. There does not appear to be any maximum to the amount of hydrogen sulfate that may be used other than any maximum that might be imposed by economic constraints.

When the hydrogen halide is hydrogen bromide, the reaction is conducted at a temperature in the range of about $+10°$ C. to about $-35°$ C., preferably about $0°$ C.

to about −35° C., in order to achieve the advantages of the invention. When the hydrogen halide is hydrogen chloride, the reaction temperature is in the range of about −10° C. to about −35° C., preferably about −25° C. to about −35° C.

The process of the invention is exothermic, so the reactants should be combined at a rate that permits control of the reaction temperature. In conducting the process it is preferred to add a mixture of the aromatic hydrocarbon and acetaldehyde to a sulfuric acid solution saturated with the hydrogen halide and to add additional hydrogen halide during the reaction. However, alternatively, the acetaldehyde and hydrogen halide can be prereacted, or the aromatic hydrocarbon can be the first charge to the reaction vessel.

The invention is particularly advantageous as a method of preparing 1-halo-1-arylethanes from aromatic hydrocarbons, such as monoalkylbenzenes and other monoalkylaromatic hydrocarbons, that have not previously been found to be capable of providing acceptable yields of such products by haloalkylation processes utilizing acetaldehyde. The process is of especial interest in the haloethylation of monoalkylbenzenes, where it has the advantage of not only minimizing the co-formation of diarylalkane by-product but of also increasing the para/ortho ratio in the product.

As is known, the products obtained by the process are useful as internal standards, intermediates for the preparation of monomers, detergents, pharmaceuticals, etc. When they are used as chemical intermediates, they may be subjected to the same reactions as have previously been used to convert them to desired products. For example, the 1-halo-1-arylethanes can be dehydrohalogenated in any known manner to provide styrenes which can then be polymerized by known techniques.

A particularly interesting application of the 1-halo-1-(4-alkylphenyl)ethanes which are prepared in a preferred embodiment of the invention is as intermediates for the preparation of ibuprofen and related pharmaceuticals. When they are used in such applications, they may be converted to the desired products in any suitable manner. For example, they may be reacted with carbon monoxide in the presence of a carbonylation catalyst and then acidified to the corresponding propionic acids as in Gardano et al., Francalanci et al., or Dynamit Nobel; or they may be reacted with an alkali metal cyanide or a tetraalkylammonium cyanide and then hydrolyzed to the corresponding propionic acids as in Palecek et al. or Tokutake. Another useful synthesis involves reacting the compounds with magnesium, carbonating the resultant Grignard reagent with carbon dioxide, and hydrolyzing the carbonated product to the propionic acid as in Miyatake et al.

The following examples are given to illustrate the invention and are not intended as a limitation thereof.

EXAMPLE I

A suitable reaction vessel was charged with 60 mL of 93% sulfuric acid, which was cooled to −3° C. and saturated with anhydrous hydrogen bromide. A solution of 7.8g of acetaldehyde and 21.3g of isobutylbenzene was fed to the reaction vessel over a period of 50 minutes at −3° C. with hydrogen bromide bubbling into the reaction mass. The reaction mass was stirred for one hour at −3° C. and then poured into ice water. Analysis showed a 1-bromo-1-(isobutylphenyl)ethane/1,1-di(isobutylphenyl)ethane mol ratio of 1.8.

EXAMPLE II

While maintaining a constant hydrogen bromide sparge, a solution of 1.2 molar proportions of acetaldehyde and one molar proportion of isobutylbenzene was added over a period of five minutes to 4.8 molar proportions of 93% sulfuric acid which had been precooled to a bath temperature of −35° C., and a reaction was conducted for 1.2 hours before being terminated. Analysis of the product showed a 1-bromo-1-(isobutylphenyl)ethane/1,1-di(isobutylphenyl)ethane mol ratio of 11.

EXAMPLE III

A suitable reaction vessel was charged with 60 mL of 93% sulfuric acid, which was cooled to −35 C and saturated with anhydrous hydrogen chloride. A solution of 7.8g of acetaldehyde and 21.3g of isobutylbenzene was fed to the reaction vessel over a period of 30 minutes at −35.C with hydrogen chloride bubbling into the reaction mass. The reaction mass was stirred for one hour at −35.C and then poured into ice water. Analysis showed a 1-chloro-1-(isobutylphenyl)ethane/1,1-di(isobutylphenyl)ethane mol ratio of 7.3.

EXAMPLE IV

Crude 1-chloro-1-(isobutylphenyl)ethane containing 47g of 1-chloro-1-(isobutylphenyl)ethane was added to a mixture of 17g of sodium cyanide in 126g of dimethyl sulfoxide (DMSO). The reaction mixture was heated to 80° C. with agitation for 10 hours, after which the DMSO and inorganic salts were removed by water washing to yield 1-cyano-1-(isobutylphenyl)ethane. The crude nitrile was reacted with excess 50% sodium hydroxide at 135.C for four hours to form the sodium salt of 2-(isobutylphenyl)propionic acid, which was then acidified and crystallized from hexane at −10.C. The para/ortho ratio of the resultant 2-(isobutylphenyl)propionic acid in hexane solution was approximately 200/1.

EXAMPLE V

While maintaining a constant hydrogen chloride sparge, a solution of 1.2 molar proportions of acetaldehyde and one molar proportion of isobutylbenzene was added over a period of two minutes to 4.8 molar proportions of 93% sulfuric acid which had been precooled to a bath temperature of −19.C, and a reaction was conducted for 1.2 hours to convert 61% of the isobutylbenzene. Analysis of the product showed a 1-chloro-1-(isobutylphenyl)ethane/1,1-di(isobutylphenyl)ethane mol ratio of 6.

COMPARATIVE EXAMPLE A

Example V was essentially repeated except that the bath temperature was 0° C., the addition time was one minute, and the reaction time was 0.2 hour. The conversion of isobutylbenzene at the end of the reaction was 64%, but the 1-chloro-1-(isobutylphenyl)ethane/1,1-di(isobutylphenyl)ethane mol ratio was only 0.8.

EXAMPLE VI

While maintaining a constant hydrogen chloride sparge, a solution of 1.2 molar proportions of acetaldehyde and one molar proportion of isobutylbenzene was gradually added to 2.5 molar proportions of 93.7% sulfuric acid which had been precooled to a bath temperature of −20 C, and a reaction was conducted for one hour. Analysis of the product showed a 1-chloro-1-(isobutylphenyl)ethane/1,1-di(isobutylphenyl)ethane mol ratio of 8.

COMPARATIVE EXAMPLE B

Example VI was essentially repeated except that the amount of sulfuric acid was decreased to 1.2 molar proportions. Analysis of the product showed a 1-chloro-1-(isobutylphenyl)ethane/1,1-di(isobutylphenyl)ethane mol ratio of only 4.

It is obvious that many variations may be made in the products and processes set forth above without departing from the spirit and scope of this invention.

What is claimed is:

1. In a process for haloethylating a monoalkylaromatic hydrocarbon by reacting it with hydrogen chloride or bromide and acetaldehyde to form a 1-halo-1-arylethane, the improvement which comprises conducting the reaction at a temperature in the range of about 0° C. to about −35° C. in the presence of at least about 1.4 mols of hydrogen sulfate per mol of the aromatic hydrocarbon and in the absence of more than about 15% by weight of water, based on the weight of the hydrogen sulfate; the temperature being not higher than about −10° C. when hydrogen chloride is employed.

2. The process of claim 1 wherein the monoalkylaromatic hydrocarbon is a monoalkylbenzene.

3. The process of claim 2 wherein the monoalkylbenzene is a hydrocarbon in which the alkyl substituent contains 1-5 carbons.

4. The process of claim 3 wherein the monoalkylbenzene is isobutylbenzene.

5. The process of claim 1 wherein the reaction is conducted in the absence of more than about 10% by weight of water, based on the weight of the hydrogen sulfate.

6. The process of claim 1 wherein the hydrogen sulfate is introduced into the reaction mixture in the form of 90-98% sulfuric acid.

7. The process of claim 6 wherein the sulfuric acid has a concentration of 93-98%.

8. The process of claim 1 wherein the amount of hydrogen sulfate is at least about 5 mols per mol of monoalkylaromatic hydrocarbon.

9. The process of claim 1 wherein hydrogen bromide is employed and the reaction temperature is in the range of about 0° C. to about −35° C.

10. The process of claim 1 wherein hydrogen chloride is employed and the reaction temperature is in the range of about −25° C. to about −35° C.

11. The process of claim 1 wherein isobutylbenzene is bromoethylated to 1-bromo-1-(4-isobutylphenyl)ethane by reacting it with anhydrous hydrogen bromide and acetaldehyde at a temperature in the range of about 0° C. to about −35° C. in the presence of at least about 5 mols of hydrogen sulfate per mol of isobutylbenzene, the hydrogen sulfate being introduced in the form of 93-98% sulfuric acid.

12. The process of claim 1 wherein isobutylbenzene is chloroethylated to 1-chloro-1-(4-isobutylphenyl)ethane by reacting it with anhydrous hydrogen chloride and acetaldehyde at a temperature in the range of about −25° C. to about −35° C. in the presence of at least about 5 mols of hydrogen sulfate per mol of isobutylbenzene, the hydrogen sulfate being introduced in the form of 93-98% sulfuric acid.

* * * * *